(12) United States Patent
Kraus et al.

(10) Patent No.: US 7,952,714 B2
(45) Date of Patent: May 31, 2011

(54) APPARATUS FOR DETECTION OF THE ACCURACY OF FORMAT OF A WEB OF CORRUGATED CARDBOARD

(75) Inventors: Helmut Kraus, Wackersdorf (DE); Markus Hausner, Püchersreuth (DE)

(73) Assignee: BHS Corrugated Machinen-und Anlagenbau, Weiherhammer (DE)

( * ) Notice: Subject to any disclaimer, the term of this patent is extended or adjusted under 35 U.S.C. 154(b) by 239 days.

(21) Appl. No.: 12/247,537

(22) Filed: Oct. 8, 2008

(65) Prior Publication Data
US 2009/0091761 A1 Apr. 9, 2009

(30) Foreign Application Priority Data
Oct. 9, 2007 (EP) .................................. 07019680

(51) Int. Cl.
*G01N 21/84* (2006.01)
(52) U.S. Cl. ....................................................... 356/429
(58) Field of Classification Search .......................... None
See application file for complete search history.

(56) References Cited

U.S. PATENT DOCUMENTS

| 5,243,402 | A | 9/1993 | Weber et al. |
| 5,857,395 | A | 1/1999 | Bohm et al. |
| 6,836,311 | B2 | 12/2004 | Hong |
| 6,836,331 | B2 * | 12/2004 | Reis et al. ............ 356/429 |

FOREIGN PATENT DOCUMENTS

| DE | 4031633 A1 | 4/1992 |
| EP | 1101601 A1 | 5/2001 |
| EP | 1757548 A1 | 2/2007 |
| WO | 0218123 A1 | 3/2002 |

* cited by examiner

*Primary Examiner* — Gregory J Toatley
*Assistant Examiner* — Amanda H Merlino
(74) *Attorney, Agent, or Firm* — Browdy and Neimark, PLLC

(57) ABSTRACT

An apparatus for detection of the accuracy of format of a web of corrugated cardboard moved in a conveying direction comprises a light source which emits a light band to the surface of the web of corrugated cardboard in a direction crosswise of the conveying direction and at an angle to the web of corrugated cardboard. A measuring camera detects the different light intensities of the light reflected by the plane portions and the profiled patterns of the web of corrugated cardboard. This electronic image in the camera is evaluated by an evaluation device for determining the distance of the profiled patterns from each other.

10 Claims, 2 Drawing Sheets

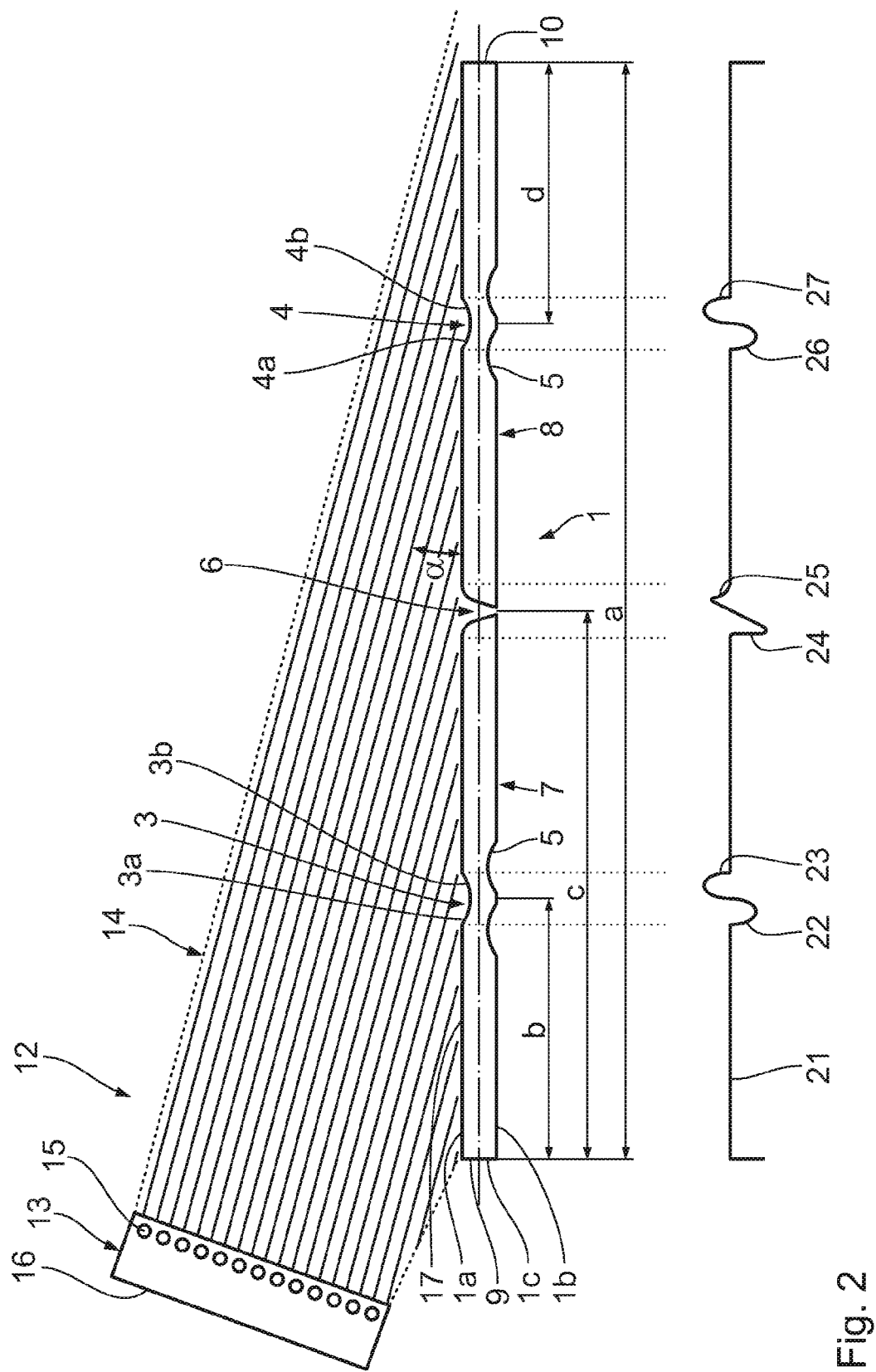

APPARATUS FOR DETECTION OF THE ACCURACY OF FORMAT OF A WEB OF CORRUGATED CARDBOARD

BACKGROUND OF THE INVENTION

1. Field of the Invention

The invention relates to an apparatus for detection of the accuracy of format of a web of corrugated cardboard moved in a conveying direction, which corrugated cardboard comprises at least an upper liner with a surface and a total width a and at least two profiled patterns of the upper liner, namely lateral edges and at least one of a longitudinal cut dividing the web of corrugated cardboard into partial webs and at least an upper groove, which profiled patterns run in the conveying direction and which profiled patterns have distances b, c, d from each other, and which corrugated cardboard has plane portions of the surface between the profiled patterns.

2. Background Art

In such an apparatus known from U.S. Pat. No. 6,836,331, two sensors are arranged on both sides of the web of corrugated cardboard, of which a first sensor is designed such as to measure the distance of the first liner from the first sensor and of which a second sensor is designed such as to measure the distance of a second liner from the second sensor. In order to detect the position of at least two profiled patterns, the two sensors are arranged relative to each other and are synchronously displaceable crosswise of the conveying direction of the web of corrugated cardboard. Downstream of the sensors is disposed an evaluation device for detecting the distance of the at least two profiled patterns from each other. The accuracy of measurement of this device is satisfactory. A disadvantage is that the constructional effort for crosswise displacement of the sensors is quite extensive and that the time required for the respective measuring process in relation to the high speed of webs of corrugated cardboard in corrugated-cardboard machines is very high.

Thus it is the object of the invention to provide an apparatus for detection of the accuracy of format of a web of corrugated cardboard moved in a conveying direction, said apparatus combining a high measuring speed and a high accuracy of measurement with a simple design.

According to the invention, this object is achieved in an apparatus of the generic type, wherein a light source emits a light band to the surface of the upper liner across the total width a thereof in a direction crosswise of the conveying direction at an angle α to the surface of the upper liner, wherein a measuring camera is arranged above the web of corrugated cardboard which absorbs light reflected by the surface and which detects the profiled patterns by means of a light intensity of the light reflected by the profiled patterns, the light intensity of which deviating from a light intensity of light reflected by plane portions of the surface, and wherein an evaluation device is connected to the measuring camera for determination of the distance b, c, d of the at least two profiled patterns from each other on the basis of the differing light intensities of the light reflected towards the measuring camera.

The gist of the invention is that the light band which is emitted to the surface of the upper liner at an angle thereto and crosswise of the conveying direction is reflected differently by the profiled patterns, in other words by the grooves and/or longitudinal cuts than by the smooth, i.e. plane portions between the profiled patterns. This allows an electronic image of the entire surface of the web of corrugated cardboard, including the profiled patterns, to be generated in a conventional measuring camera, the electronic image being evaluated in a correspondingly programmed computer serving as evaluation device, which allows to determine the respective, exact actual value of the distances of the individual profiled patterns from each other.

By the measures wherein on both sides of the web of corrugated cardboard is arranged in each case one reference point with a constant distance f from each other whose distance g from each other is continuously detected by the measuring camera, it is attained that temperature-related measuring errors in the camera can be compensated. Thus, the camera constantly receives an exact reference value for the distance between the two reference points which allows for numerical compensation of measuring errors.

The distance of the camera from the surface of the web of corrugated cardboard should be as large as possible. The distance is limited by constructional conditions in factory buildings and the like. The distance should however be chosen at least such that for the distance e of the measuring camera from a measuring line, formed by the incidence of the light band on the surface of the web of corrugated cardboard, relative to the total width a of the web of corrugated cardboard, applies $e \geq a$.

Further features, advantages and details of the invention will become apparent from the ensuing description of an embodiment, taken in conjunction with the drawing.

BRIEF DESCRIPTION OF THE DRAWINGS

FIG. 2 shows a cross-sectional view of the apparatus according to FIG. 1.

DESCRIPTION OF THE PREFERRED EMBODIMENT

Figure 1:
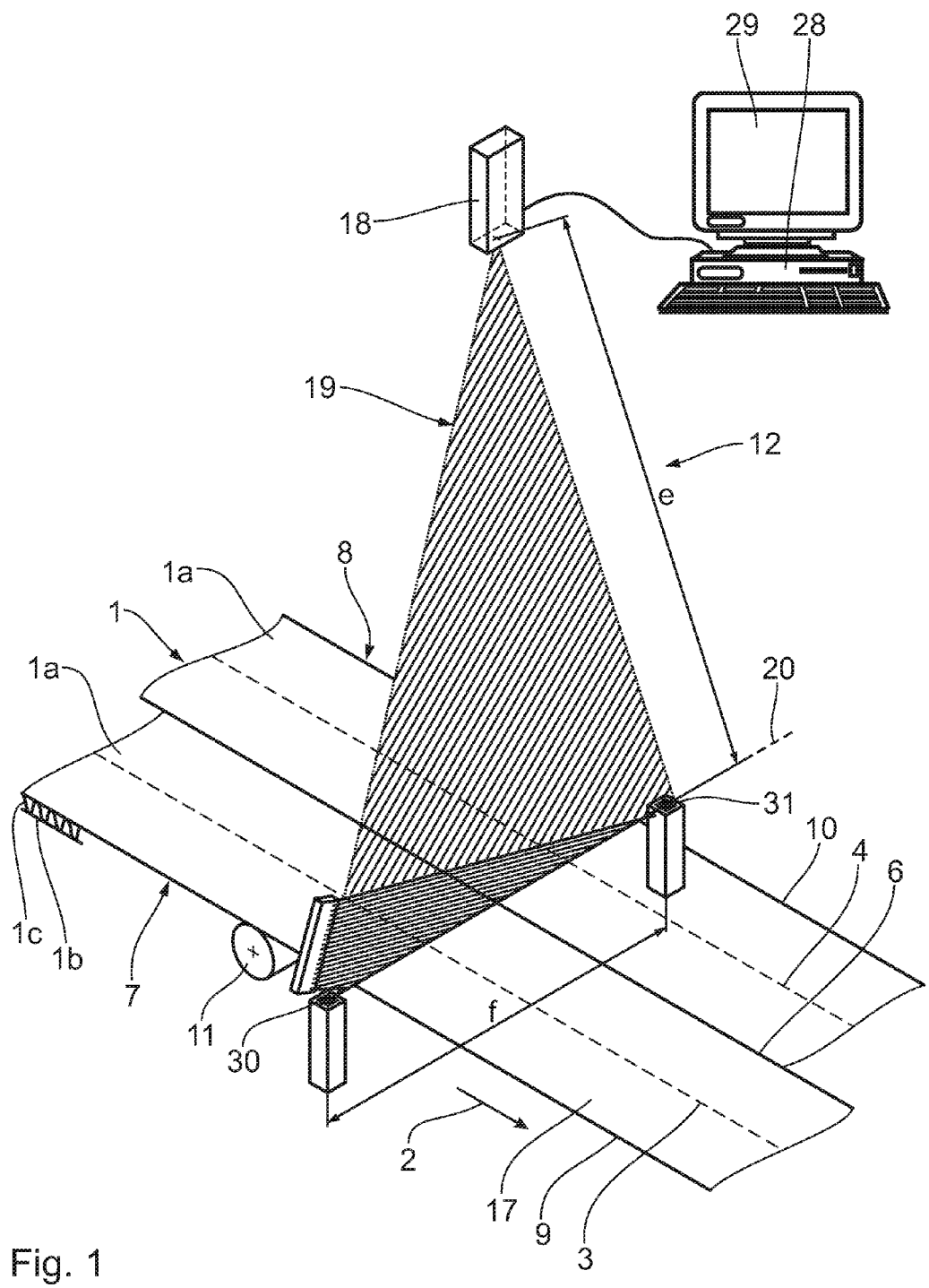
FIG. 1 shows a schematic perspective view of an apparatus for detection of the accuracy of format of a web of corrugated cardboard.

FIGS. 1 and 2 show a schematic view of a web of corrugated cardboard 1 which may however also be a conventional web of cardboard. The web of corrugated cardboard 1 conventionally comprises at least an upper smooth liner 1a and a lower, likewise smooth liner 1b between which is disposed a corrugated paper web 1c which is glued to the liners 1a and 1b. In the course of its production, the web of corrugated cardboard 1 is located on an apparatus for producing corrugated cardboard, strictly speaking downstream of a grooving and longitudinal cutting arrangement (not shown) when seen in the conveying direction 2, as it is for example shown and described in EP 0 692 369 B1 (corresponding to U.S. Pat. No. 5,857,395) which is explicitly referred to. In this arrangement, the web of corrugated cardboard 1 has been provided with upper grooves 3, 4 running in the conveying direction 2 and lower counter grooves 5 allocated thereto. In this arrangement, the web of corrugated cardboard 1 has furthermore been provided with a longitudinal cut 6, running in the conveying direction 2, by means of which the web of corrugated cardboard 1 has been divided into two partial webs 7, 8. In the mentioned grooving and longitudinal cutting arrangement, the web of corrugated cardboard 1 has furthermore been trimmed laterally in order to have an exactly defined total width a between its outer, trimmed lateral edges 9, 10.

The web of corrugated cardboard 1 is guided across a perfectly cylindrical roller 11 so as to be completely plane, in other words even, when seen crosswise of the conveying direction 2. Downstream of the roller 11 in the conveying direction 2 is arranged an apparatus 12 for detection of the accuracy of format by means of which the relevant width dimensions of the web of corrugated cardboard 1 are detected. The width dimensions include for example the distance b of the groove 3 from the lateral edge 9, the distance c of the longitudinal cut 6 from the lateral edge 9 and the distance d of the groove 4 from the adjacent lateral edge 10. Naturally, the distances of the grooves 3, 4 from each other or from the longitudinal cut 6 or all distances from only one lateral edge 9 or 10 may principally be detected as well. This only depends on the evaluation yet to be described.

The apparatus 12 for detection of the accuracy of format comprises a light source 13 which emits a light band 14 whose light beams are substantially parallel to each other. Such a light source 13 may for example consist of a plurality of LEDs 15 which are arranged in a straight row in a corresponding longitudinal housing 16 and emit approximately parallel light. Such LEDs are conventionally available. As in particular illustrated by FIG. 2, the light source 13 is arranged laterally of the web of corrugated cardboard 1 in a way that the light band 14 hits the web of corrugated cardboard 1 at a small angle α between the light band 14 and the plane surface 17 of the web of corrugated cardboard 1. The angle α is such that $5° \leq α \leq 30°$ applies.

Above the web of corrugated cardboard 1, strictly speaking centrally above the web of corrugated cardboard 1, is arranged a digital measuring camera 18 which, as indicated in FIG. 1, absorbs the light 19 reflected by the surface 17 of the web of corrugated cardboard 1. The measuring camera 18 needs to have a very high resolution. The distance e of the camera 18 from the measuring line 20 defined by the incidence of the light band 14 on the surface 17 of the web of corrugated cardboard 1 is at least equal to the total width a of the web of corrugated cardboard 1 but even larger, if possible. If the constructional conditions do not allow the camera to be arranged vertically above the measuring line 20, the plane defined by the measuring line 20 and the camera 18 may also be inclined in the conveying direction 2 or opposite to the conveying direction 2.

The light band 14 hitting the surface 17 at an angle thereto is reflected differently by the grooves 3, 4 and the longitudinal cut 6 than by the plane portions of the surface 17. FIG. 2 shows the intensity pattern of the light reflected towards the camera in relation to the width of the web of corrugated cardboard 1. In the region between the lateral edge 9 of the partial web 7 and the groove 3, the light is reflected uniformly towards the camera. The light intensity pattern of the light 19 reflected towards the measuring camera 18 is thus linear. In the downward portion 3a of the groove facing the mentioned portion 21 of constant light intensity of the light 19, the incidence of light—in relation to a width unit of the web of corrugated cardboard 1—is lower than before, in other words less light per width unit is reflected towards the camera 18 in this downward portion 3a of the groove 3. The light intensity of the light 19 reflected towards the measuring camera 18 thus shows a portion 22 that decreases in relation to the linear portion 21. In the portion 3b of the groove 3 that is directed upwardly in relation to the direction of the light band 14, more light per width unit of the web of corrugated cardboard 1 is reflected towards the camera 18; the result is an increased light intensity 23.

In the region of the longitudinal cut 6, there is at first a greatly reduced light intensity 24 and then a slightly increased light intensity 25. Corresponding to the groove 3, there is a reduced light intensity 26 in the downward portion 4a of the groove 4 while in the upward portion 4b of the groove 4, there is an increased light intensity 27 of the light 19 reflected towards the measuring camera 18. FIG. 2 shows that there is a uniform light intensity in all regions of the surface 17 between the grooves 3, 4 and the longitudinal cut 6 as well as between the lateral edges 9, 10 and the adjacent grooves 3, 4. The center of the light intensity portions 22, 23 or 24, 25 or 26, 27, respectively, thus exactly corresponds to the center of the groove 3 or of the longitudinal cut 6 or of the groove 4, respectively; a corresponding image is generated in the camera 18. No light is reflected at the lateral edges 9, 10; the entire light intensity pattern according to FIG. 2 thus only extends across the exact width a of the web of corrugated cardboard 1.

Generated electronically in the camera 18, the exact image of the surface 17 with the exact positions of the grooves 3, 4 and the longitudinal cut 6 is transmitted to a computer 28 serving as evaluation device in which the actual values of the distances b, c, d are determined and displayed for example on a monitor 29 serving as display device. If there is an aberration from predetermined desired values, the operator may readjust the mentioned grooving and longitudinal cutting arrangement, if necessary. The desired values may naturally also be stored in the computer 28 for comparison with the mentioned actual values, which may be useful for an automatic control of the grooving and longitudinal cutting arrangement. The comparison of the actual values with the desired values takes place by means of a data interface for controlling the grooving and longitudinal cutting arrangement. In this process, the desired values are transmitted automatically.

On both sides of the web of corrugated cardboard 1 are arranged stationary reference points 30, 31 which are in line with the measuring line 20. These reference points 30, 31 have an exact fixed distance f from each other. These reference points 30, 31 are detected continuously by the measuring camera 18 as well. Since in particular small temperature variations may lead to minute distortions in the objective of the measuring camera 18 or in other regions relevant for the accuracy of measurement of the measuring camera 18, such temperature variations result in measurement errors. If in each case the exact distance f of the reference points 30, 31 is detected, the described measuring values, i.e. the position of the grooves 3, 4 and of the longitudinal cut 6 and therefore the corresponding distances b, c, d, can be corrected numerically. Calculation errors with respect to the distances b, c, d can thus be kept in the range of below 0.5 mm.

What is claimed is:

1. An apparatus for detection of the accuracy of format of a web of corrugated cardboard moved in a conveying direction, said web of corrugated cardboard comprising at least an upper liner with a surface and a total width a, said at least an upper liner comprising at least three profiled patterns, said at least three profiled patterns comprising a first lateral edge, a second lateral edge and at least one of a longitudinal cut dividing the web of corrugated cardboard into partial webs and at least one upper groove, said three profiled patterns extending in the conveying direction and said three profiled patterns being spaced apart at distances b, c, d from each other, wherein the distance b is a distance between said first lateral edge and a first one of said at least one of the longitudinal cut and the at least one upper groove and wherein the distance c is a distance between said first lateral edge and a second one of said at least one upper groove and the longitudinal cut and wherein the distance d is a distance between said second lateral edge and a third one of the at least one of the longitudinal cut and said at least one upper groove, and said corrugated cardboard having plane portions of the surface between the three profiled patterns, said apparatus comprising a light source which emits a light band toward the surface of the upper liner across the total width a thereof in a direction crosswise of the conveying direction at an angle α with respect to the surface of the upper liner, a measuring camera arranged above the web of corrugated cardboard which absorbs light (19) reflected by the surface and which detects the three profiled patterns by detecting light intensity of the light reflected by the three profiled patterns, the light intensity reflected by the three profiled patterns differing from a light intensity of light reflected by the plane portions of the surface, and an evaluation device connected to the measuring camera for determination of the distances b, c, d of the at least three profiled patterns from each other on the basis of the differing light intensities of the light reflected towards the measuring camera.

2. An apparatus according to claim 1, wherein on both sides of the web of corrugated cardboard is arranged in each case one reference point with a constant distance f from each other whose distance f from each other is continuously detected by the measuring camera.

3. An apparatus according to claim 1, wherein a distance e between the measuring camera and a measuring line, formed by the incidence of the light band on the surface of the web of corrugated cardboard, relative to the total width a of the web of corrugated cardboard e ≧ a applies.

4. An apparatus according to claim 1, wherein the light source is arranged laterally of the web of corrugated cardboard.

5. An apparatus according to claim 1, wherein for the angle α, $5° \leq α \leq 30°$ applies.

6. An apparatus according to claim 1, wherein the light source emits approximately parallel light.

7. An apparatus according to claim 1, wherein the light source is formed by a plurality of LEDs which are arranged one above the other in a straight row.

8. An apparatus for detection of the accuracy of format of a web of corrugated cardboard moved in a conveying direction, said web of corrugated cardboard comprising at least an upper liner with a surface and a total width of the web of corrugated cardboard, said at least an upper liner comprising at least three profiled patterns, said at least three profiled patterns comprising a first lateral edge, a second lateral edge and at least one of a longitudinal cut dividing the web of corrugated cardboard into partial webs and at least one upper groove, said three profiled patterns extending in the conveying direction and said three profiled patterns being spaced apart at varying distances from each other, and said corrugated cardboard having plane portions of the surface between the three profiled patterns, said apparatus comprising:

a light source which emits a light band toward the surface of the upper liner across the total width thereof in a direction crosswise of the conveying direction at an angle α with respect to the surface of the upper liner, a measuring camera arranged above the web of corrugated cardboard which absorbs light (19) reflected by the surface and which detects the three profiled patterns by detecting light intensity of the light reflected by the three profiled patterns, the light intensity reflected by the three profiled patterns differing from a light intensity of light reflected by the plane portions of the surface, and an evaluation device connected to the measuring camera for determination of the distances of the at least three profiled patterns from one another on the basis of the differing light intensities of the light reflected towards the measuring camera.

9. An apparatus according to claim 8, wherein on both sides of the web of corrugated cardboard is arranged in each case one reference point with a constant distance from each other, and wherein the measuring camera continuously detects positions of the reference points.

10. An apparatus according to claim 8, wherein a distance between the measuring camera and a measuring line, formed by the incidence of the light band on the surface of the web of corrugated cardboard, is greater than or equal to the total width of the web of corrugated cardboard.

* * * * *